United States Patent [19]

Barkalow et al.

[11] 4,273,114
[45] Jun. 16, 1981

[54] CARDIOPULMONARY RESUSCITATOR, DEFIBRILLATOR AND MONITOR

[75] Inventors: Clare E. Barkalow, Comstock Park, Mich.; James O. Elam, Chicago, Ill.

[73] Assignee: Michigan Instruments, Inc., Grand Rapids, Mich.

[21] Appl. No.: 96,659

[22] Filed: Nov. 23, 1979

Related U.S. Application Data

[63] Continuation-in-part of Ser. No. 952,656, Oct. 19, 1978, Pat. No. 4,198,963.

[51] Int. Cl.³ .............................................. A61N 1/36
[52] U.S. Cl. .................................. 128/53; 128/419 D
[58] Field of Search ............................. 128/53, 419 D

[56] References Cited

U.S. PATENT DOCUMENTS

| 3,326,207 | 6/1967 | Egan | 128/642 |
|---|---|---|---|
| 3,461,860 | 8/1969 | Barkalow | 128/53 |
| 3,461,861 | 8/1969 | Barkalow et al. | 128/53 |
| 3,716,059 | 2/1973 | Welborn et al. | 128/419 D |
| 3,837,347 | 9/1974 | Tower | 128/785 |
| 4,082,090 | 4/1978 | Harrigan | 128/28 |
| 4,088,138 | 5/1978 | Diack et al. | 128/419 D |
| 4,090,518 | 5/1978 | Elam | 128/351 |

FOREIGN PATENT DOCUMENTS 1535612  7/1968  France ..................................... 128/53

OTHER PUBLICATIONS

Schaudinschky et al., "Medical and Biological Engineering" vol. 7, No. 3, May 1969, pp. 341-343.

Primary Examiner—William E. Kamm
Attorney, Agent, or Firm—Price, Heneveld, Huizenga & Cooper

[57] ABSTRACT

A reciprocal cardiac compressor is provided for cyclically compressing a patient's chest. Preferably a resuscitator is also provided for ventilating the patient's lungs. The compressor includes a reciprocal compressor pad positioned anterior to the patient's heart and a stationary base positioned posterior to the patient's heart. An anterior electrode is disposed on the face of the compressor pad for compression between the compressor pad and the patient's sternum and a posterior electrode is disposed on the base of the compressor for compression between the base and the patient's back. A cardiac defibrillator is connected between anterior and posterior electrodes for establishing a defibrillating electric current therebetween. A monitor is connected to the anterior and posterior electrodes for monitoring the electrical activity of the patient's heart. Means for snychronizing the defibrillator and the compressor is provided comprising a pressure sensitive switch for synchronizing the defibrillator and compressor such that defibrillating current is applied to the patient's heart only during a systolic portion of the compression cycle of the compressor.

29 Claims, 8 Drawing Figures

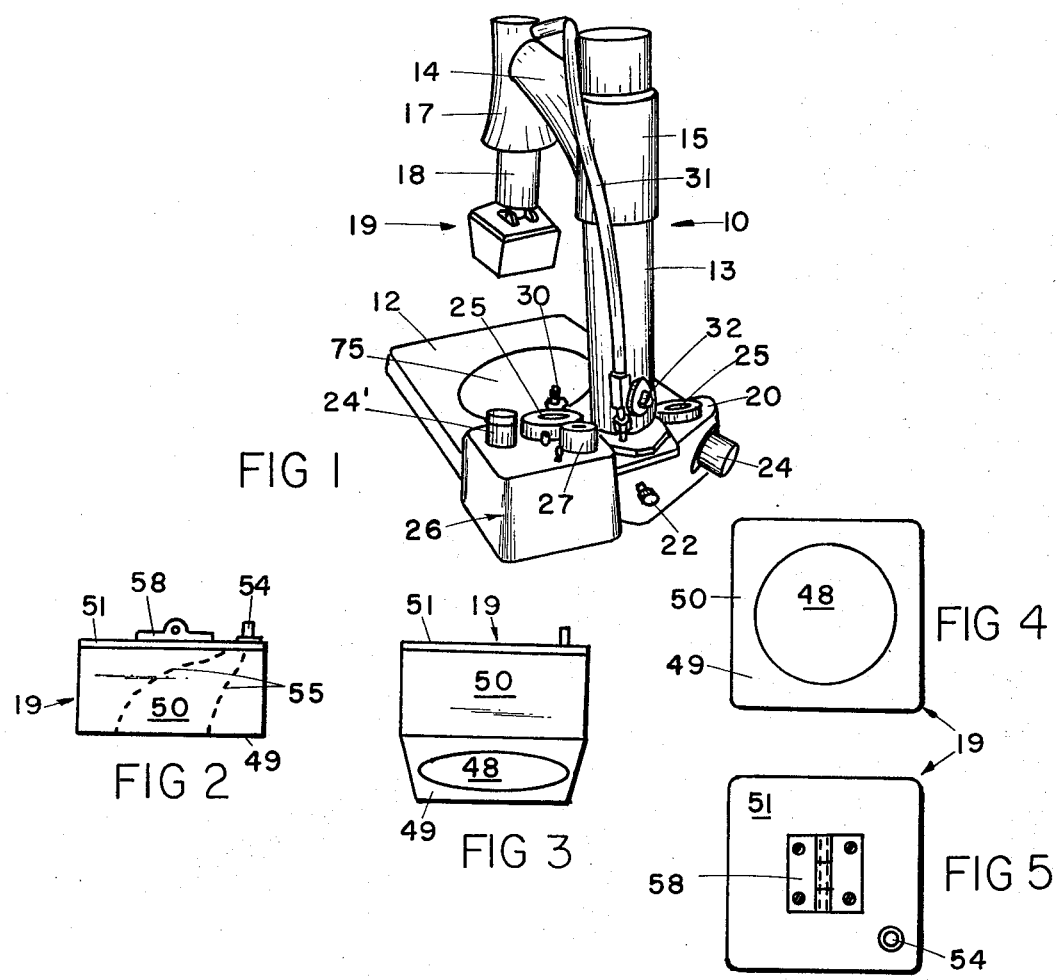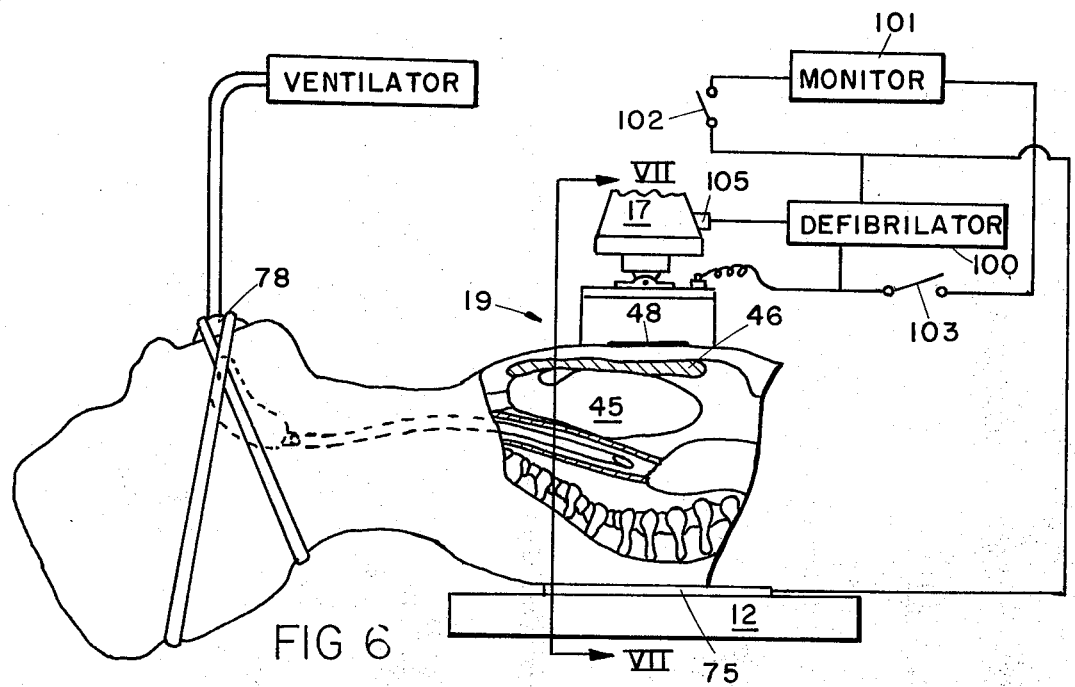

CARDIOPULMONARY RESUSCITATOR, DEFIBRILLATOR AND MONITOR

This application is a continuation-in-part of United States patent application Ser. No. 952,656 filed Oct. 19, 1978 and now U.S. Pat. No. 4,198,963 entitled CARDIOPULMONARY RESUSCITATOR, DEFIBRILLATOR AND MONITOR.

BACKGROUND OF THE INVENTION

This invention relates generally to cardiopulmonary resuscitation defibrillation and monitoring apparatus and, more particularly, to a combination cardiac compressor, lung ventilation, defibrillator and heart monitor apparatus.

External cardiac compression can be effectively employed for obtaining perfusion by causing forced pumping of blood from a temporarily stopped heart. This is achieved by constant cyclic external compression of the heart (systole) for a short time period followed by pressure release to allow heart expansion (diastole) for a short time period. To achieve proper heart compression by external force, the breast bone is forced toward the backbone of the patient while the patient's back is rigidly supported.

Although forced pumping of blood is essential for a patient whose heart has stopped, this is only part of the continuous treatment necessary, since when the heart stops, breathing stops also. Hence, when external mechanical or manual cardiac compression is presently employed, simultaneous, sustained cyclic, mechanical or mouth to mouth ventilation is also important to cyclically inflate the lungs for oxygenization of the blood. According to accepted medical practice, the lungs are ventilated or inflated during the diastole period of the compression cycle. Whether carried out mechanically or manually, these techniques comprise what is commonly referred to as cardiopulmonary resuscitation or CPR. However, CPR is only supportive therapy designed merely to maintain cell viability or structure. CPR alone will normally not restart a heart that has stopped or which is in ventricular fibrillation. Definitive therapy such as defibrillation by electrical shock is normally necessary to restart the normal functioning of the heart.

In the prior art, certain disadvantages existed when such supportive and definitive therapy were combined. When applying supportive therapy, it is extremely important that there be no interruptions. In the case of manual CPR where chest compression is being performed manually by the application of force by the rescuer's hands, interruptions are presently necessary to monitor the patient's EKG and to apply electrical defibrillation shocks. In the first case, supportive therapy must be interrupted because of distortion in the patient's EKG produced by the rescuer. This distortion or noise is generated from the rescuer's own EKG and from electrical signals generated in the rescuer's muscles as he applies chest compression. This distortion or noise is high enough to completely obscure the patient's EKG and must be interrupted during the time that the patient's EKG is being assessed. This is an interruption which is inevitable in the manual CPR technique. Furthermore if the patient requires electrical defibrillation, then at that time, in the manual technique, the hands must be taken off because of the risk of giving a shock to the rescuer. Also, generally speaking, after a heavy external defibrillation shock, a substantial time period must pass before the oscilloscope and the circuitry within the oscilloscope or chart of the EKG monitor returns to normal. Sometimes it takes several seconds for the equipment to clear and provide a check on the electrical activity of the patient's heart and during this time, the patient is left unsupported.

When using one of the many standard commercially available mechanical massagers, there is often room on the chest to place defibrillation paddles while external cardiac compression is being performed. If the compressor is pneumatic rather than electrically driven, distortion in the patient's EKG is minimal and a useful signal can be obtained without interruption in supportive therapy. Thus, it is possible to give defibrillation shocks while such a CPR unit is running. However, for some reason there has been a reluctance on the part of the rescuers to use this technique, and rescuers in the past have had a tendency to shut the CPR unit off during defibrillation and monitoring. This is probably due to the fact that the rescuer carrying out the operation would be standing over the patient with some risk of his being in contact with the equipment or with the patient. Thus, even though distortion caused by pneumatically driven CPR equipment is minimal and the signal normally obtained during CPR is adequate to make a judgment as to whether the patient is in cardiac arrest or not, many rescuers insist on shutting off CPR equipment during defibrillation and monitoring.

The most common definitive therapy in the prior art is the use of a defibrillation shock for restarting a heart that has stopped or a heart that has gone into ventricular fibrillation. However, the conventional external electrodes used in the prior art are placed on the patient's chest and a disproportionately large amount of the current applied to the patient's chest never flows through the heart. Accordingly, the power requirements of prior art defibrillators are quite high and most prior art units are bulky and ill-suited to portability. Thus, it is often not possible to apply such definitive therapy to the patient until the patient has reached a hospital. Furthermore, since a disproportionate amount of energy must be applied to the patient's chest to cause that small percentage of electrical energy flowing through the heart to be sufficient to defibrillate the heart, electrical defibrillation, as carried out in the prior art, with external electrodes, is a traumatic event both for the heart and other portions of the patient's body.

Front to back defibrillation techniques are found in the prior art wherein first and second defibrillator electrodes are disposed anterior and posterior to the patient's heart on the patient's chest and back, respectively. However, none of these arrangements provide for simultaneous application of the cardiac massage because of the danger of shock to the individual applying compressive force to the patient's chest, and without simultaneous cardiac compression these defibrillation techniques provide no substantial reduction in the power of the defibrillation shock applied. Furthermore, these arrangements do not solve the aforementioned problem of interrupting supportive techniques during monitoring or defibrillation.

SUMMARY OF THE INVENTION

These and other problems in the prior art are solved by provision of a cardiac compressor and defibrillator comprising a reciprocal cardiac compressor for cyclically compressing a patient's chest. The cardiac compressor includes a reciprocal compressor pad normally positioned anterior to the patient's heart such that the pad contacts the patient's sternum. An anterior electrode is disposed on the face of the compressor pad for compression between the compressor pad and the patient's sternum. The compressor also includes a stationary base which is positioned behind the patient's back. A posterior electrode is disposed on the base for compression between the base and the patient's back. A cardiac defibrillator is connected to the anterior and posterior electrodes for establishing a defibrillating electric current therebetween. Means are provided for synchronizing the defibrillator and compressor, whereby defibrillating current is applied to the patient's heart only during a systolic portion of the compression cycle of the compressor.

With this arrangement, supportive therapy remains uninterrupted during such definitive therapy as monitoring and the application of electrical defibrillation shock. Furthermore, since electrical defibrillation shocks are now applied with anterior and posterial electrodes during the systole, or the point of maximum compression during the compression cycle, a substantial reduction in the power requirements of the defibrillator is achieved. This reduction in the power requirements of the defibrillator is achieved since anterior and posterior electrodes are centered over the heart and power is applied while these electrodes are compressed on the chest and back, when the current path is shortest, and when electrical contact is best. When the electrodes so positioned during the systole portion of the compressor cycle, more of the current applied therebetween flows through the heart. Thus, a smaller amount of electrical energy need now be applied to generate a sufficient defibrillation current in the heart, and electrical defibrillation becomes a less traumatic event, both to the heart muscle and to other parts of the body. Furthermore, the reduction in the power requirements of the defibrillator makes possible a smaller, simpler, lighter and more portable lower power defibrillators that are less expensive and which may be more easily carried on site by the rescuer.

In general, as monitoring electrodes are placed closer to the heart, stronger monitoring signals and higher signal noise ratios are achieved. The posterior electrode working in conjunction with the anterior electrode give a strong signal suitable for monitoring the heart and identifying gross arrhythmias such as ventricular fibrillation. Therefore, monitoring of the heart for gross arrhythmias and periodic defibrillation of the heart may be carried out without interruption of supportive therapy such as cardiac compression and ventilation of the lungs.

BRIEF DESCRIPTION OF THE DRAWINGS

FIG. 1 is a perspective view of a pneumatically operated combined cardiac compressor and ventilator of the present invention.

FIG. 2 is an elevational view of a compressor pad constructed according to the present invention.

FIG. 3 is a perspective view of a compressor pad constructed according to the present invention.

FIG. 4 is a bottom view of a compressor pad constructed according to the present invention.

FIG. 5 is a top view or plan view of a compressor pad constructed according to the present invention.

FIG. 6 is a schematic representation of the cardiopulmonary resuscitator defibrillator and monitor of the present invention and a fragmentary sagital section illustrating the application of the present invention to the human body.

DESCRIPTION OF THE PREFERRED EMBODIMENTS

Figure 7:
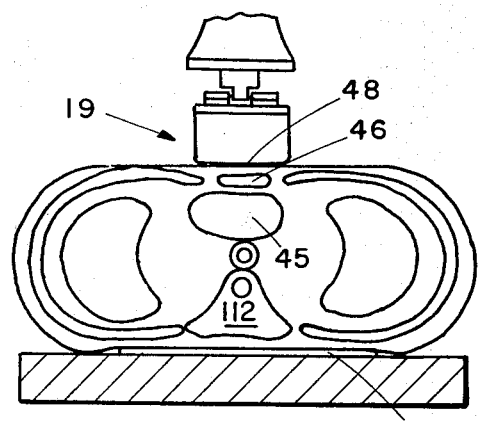
FIG. 7 is a sectional view of the human body and the apparatus of the present invention taken along line VII—VII of FIG. 6 during a diastole portion of the compressor cycle.

Referring now to FIG. 1, a combination cardiac compressor and ventilator or cardiopulmonary resuscitator unit is illustrated at 10. The CPR unit includes a platform or base 12 for supporting the back of a patient, a removable upstanding column or support 13 and an overhanging beam or arm 14 mounted to column support 13 with a releasable collar 15. The outer end of arm 14 includes a pneumatic power cylinder 17, an extendable plunger piston 18 and a compressor pad 19 for contacting and compressing a patient's sternum. The piston plunger 18 and the compressor pad 19 are pneumatically operable to shift towards the platform 12 to compress the sternum and thus the heart of the patient resting in the supine position on the platform 12. The piston and pad return with the normal expansion of the patient's chest. The platform 12 includes a thick hollow end 20 in which the support 13 is removably mounted and which includes an internal chamber that encloses a control valve assembly at 22. The control valve assembly repetitively applies pressure to the power cylinder to create a cyclical compression cycle. Protruding from the platform portion 20 is a pressure regulator knob 24 for controlling the pressure of the output of control valve assembly 22. A pressure indicating gauge is disposed at 25. A ventilator subassembly is disposed at 26 and is integrally mounted with the compressor with the exception of a breathing hose normally connected to air outlet 27 and a mask or tube for directing oxygen enriched air into the patient's lungs. A pressure regulator knob 24' and a gauge 25' are used to control the air pressure applied to the patient's lungs during ventilation. The CPR unit used herein is essentially like that shown in U.S. Pat. No. 3,461,860 to Clare. E. Barkalow and the disclosure of that patent is incorporated herein by reference.

According to current CPR protocol the cardiac compressor operates at a relatively high pulse rate. The ventilator operates at a much slower pulse rate. For example, a ratio of compressor to ventilator cycles is commonly 5:1. When combining the two, means is provided to cause a ventilation cycle to occur only every multiple of compressor cycles. The compressor cycles are controlled by the aforementioned control valve 22. Periodic output pulses of oxygen from the control valve are allowed to pass to the ventilator 26. These pulses activate a programmer valve within the ventilator to turn it on, and the duration of the "on" cycle is regulated by a timer control.

One of the advantages of this type of apparatus is that both the cardiac compressor and the ventilator of the CPR unit are pneumatically operated and pneumatically controlled. Once the device is set up, the only power source required is an external source of compressed gas, normally oxygen, which is connected to the unit via a gas hose attached to fixed connector 30. This supply of pressurized oxygen operates the entire CPR unit. Pressurized oxygen passes through the compressor control valve assembly 22, inside the cardiac compressor platform, and then through hose 31 that extends to the upper end of cylinder 17. A manual shut-off valve 32 may be provided to turn off the cardiac compressor manually while allowing the ventilator unit 26 to still operate on a cyclical basis. Oxygen also passes to a programmer, not illustrated, that is a pneumomechanical device serving to periodically open a passageway for a flow of oxygen to the ventilator at regular intervals after a specific number of compression cycles of the cardiac compressor. The programmer can be preset to provide flow of oxygen to the ventilator at regular multiples of intervals, usually 1 out of 5 of the cardiac compressor cycles, since the lungs should be ventilated only once every multiple of cardiac compressions. According to the presently accepted medical teachings, the programmer is set to turn on the ventilator during cardiac diastole, that is, when compressor cylinder pressure is zero and the chest is free to expand. When the ventilator program determines that the correct number of compression cycles has passed, a flow of ventilating oxygen occurs from outlet 27 which is directed into the patient's lung with a mask, tube or the like and an interconnecting hose. Further details of the structure and operation of a CPR unit suitable for use with the present invention may be obtained from the aforementioned Barkalow patent.

Referring now also to FIGS. 2, 3, 4 and 5, details of the cardiac compressor pad 19 of the present invention are illustrated. The cardiac compressor pad 19 is connected to and is actuated by the CPR unit 10 for compressing the patient's sternum and thus compressing the patient's heart between the sternum and spine. The compressor pad 19 as best illustrated in FIG. 6, is positioned anterior to the patient's heart 45 in contact with the lower portion of the patient's sternum 46. An anterior electrode 48 is disposed on a face 49 of the compressor pad 19 for compression between the compressor pad 19 and the patient's sternum 46. The body 50 of the compressor pad 19 is preferably molded from an elastomer of a semi-rigid type. The body 50 is mounted on a planar support 51. The face 49 of the compressor pad 19 preferably extends over an area somewhat greater than that of conventional external compressor pads and an area somewhat greater than the manual "heel of hand" contact area normally available when the manual CPR technique is applied. The area of face 49 is preferably several times larger than the normal manual "heel of hand" contact area.

The anterior electrode 48 covers a relatively large area of the face 49 and is preferably five square inches or more in area. Electrode 48 is isolated electrically from all metal parts of the CPR assembly except that it is electrically connected to a terminal 54 disposed at the top of the assembly by multiple internal flexible leads shown in phantom at 55 in FIG. 2. The electrode 48 is preferably flexible to conform to the shape of the patient's chest and sternum and a metal mesh screen electrode vulcanized to the face 49 of the compressor pad 19 is preferred. Gold plated brass mesh screens and silver mesh screens have both been found suitable. However, a suitable conductive elastomer may also be employed for the body 50 of compressor pad 19, or for at least the face 49 of the body 50 to act as the electrode 48. In the case where the anterior electrode is integrally formed in the body of the compressor pad 19 the electrode must be electrically insulated from the rest of the CPR unit.

The planar support 51 for the body 50 of compressor pad 19 includes a hinge or pin-type connection 58 so that the compressor pad 19 may be pinned to the piston 18 of the CPR unit 10. This hinged connection is preferable since the patient's sternum 46 is not always horizontally oriented when the patient is in the supine position as illustrated in FIG. 6. This hinged, or pinned connection allows the compressor pad 19 to more closely follow or conform to the patient's chest. In an effort to further reduce the trauma of external cardiac compression and to increase the compliance and conductivity of electrode 48, the base 49 of the body 50 of compressor pad 19 is preferably molded to conform to the outline of a typical human chest. The body 50 of flexible elastomer then further acts to accommodate minor variations in the topography of each patient's chest.

Referring to FIGS. 1 and 6 it is illustrated that the base 12 of the compressor is provided with a posterior electrode 75. The posterior electrode is disposed on the face of the base 12 for compression between the base 12 and the bare back of the patient to create good ohmic contact therebetween. Like the anterior electrode 48, the posterior electrode may be fabricated from a silver or gold plated mesh screen or may be integrally formed in the base 12. In any case, the posterior electrode must be electrically insulated from the rest of the CPR unit. Although not illustrated herein, the base 12 may be contoured to more closely conform to the patient's back and the electrode 75 may be disposed on an elastomer pad which is secured to the base 12 to insure that the electrode closely conforms to the patient's back and a good ohmic contact is created therebetween. The area of the posterior electrode 75 is somewhat larger than the area of the anterior electrode 48 and is generally approximately 10 square inches or more.

FIG. 6 illustrates that the ventilator may supply oxygen to inflate the patient's lungs through an esophago-pharyngeal airway 78. An esophago-pharyngeal airway is disclosed in U.S. Pat. No. 4,090,578 entitled ESOPHAGO-PHARYNGEAL AIRWAY to James O. Elam. The disclosure of the aforementioned patent is hereby incorporated by reference. However, use of such an airway is not necessary and any suitable airway, cuff, mask or other oral seal suitable for use with a ventilator, may be employed. The present embodiment of the invention has an advantage over embodiments disclosed in our parent application since many paramedics and medical technicians are not trained to insert an esophago-pharnygeal airway and according to the present invention such an airway is not needed to place a defibrillating electrode posterior to the heart. Although use of a posterior electrode disposed on the base of the compressor requires the application of more electrical power to the defibrillating electrodes the amount of power required is still substantially lower than that required when using conventional chest mounted electrodes, because of the proximity of the anterior and posterior electrodes to the heart during the systolic portion of the compressor cycle.

As further illustrated in FIG. 6, the anterior and posterior electrodes 48 and 75, respectively, are connected to a defibrillator 100 and/or an EKG monitor 101. It it to be understood that suitable switching means 102 and 103 will be used to isolate the monitor from the defibrillator during defibrillator operation, although this is commonly included within combined monitor/defibrillator units in common use. The invention further includes means for synchronizing the defibrillator and the compressor, preferably comprising a pressure sensitive switch 105 for sensing pneumatic pressure within the power cylinder 17 of the CPR unit 10. The pressure switch 105 acts to disable the defibrillator unit except when pressure within power cylinder 17 reaches a predetermined value. This ensures that when the defibrillating counter shock is only applied to the patient's heart during compression of the patient's heart, or during a systolic portion of the compressor cycle. Preferably the pressure switch is set to allow the application of a defibrillating shock only during, or close to, the period of maximum compression in the compressor cycle. However, if the pressure switch is adjustable, the time in the compression cycle during which the defibrillating shock may be applied, may be varied. Adjustability of the pressure switch is also important where it is desirable to only apply the defibrillating shock at the point of maximum compression since the maximum compression pressure will vary with different patients.

It is to be understood that standard defibrillator and monitor circuits may be employed with the present invention although, because of the certain unique advantages presented by the present invention, a defibrillator of less power than standard defibrillator circuits may be employed. Standard defibrillating circuits include hand-held electrodes or paddles having defibrillating control switches disposed thereon. These standard, commercially available, defibrillating circuits could be modified for use with the present invention by wiring these standard paddle switches or their equivalents in series with pressure actuated switch 105 such that manual actuation of the defibrillator is effective only during the time period when the pressure in power cylinder 17 closes switch 105, indicating that the compressor is in a systolic portion of the compressor cycle.

OPERATION

Referring now to FIGS. 1 and 6, to employ the apparatus of the present invention with a patient requiring cardiac compression for blood perfusion and lung ventilation or blood oxygenization, all clothing is removed from the patient's torso, and the patient is placed in the illustrated position (FIG. 6) with his back on platform 12. The cardiac compressor is then adjusted so that the compressor pad 19 is immediately over the lower portion of the patient's sternum 46. Arm 14 of the cardiac compressor is vertically adjusted on columnar support 13 so that the pad 19 contacts the breast bone or sternum when the pad and plunger are in the raised position. A gas supply hose from a conventional source of pressurized oxygen is then connected to the unit at 30. Initially, the cardiac compressor equipment is actuated and adjusted to create the desired chest deflection by adjustment of knob 24 and monitoring of the amount of sternal deflection, preferably set at 20% of the patient's anterior-posterior chest dimension. In addition, a suitable oral seal, mask or the like is used to connect the ventilator to the patient's lungs. At this point, the ventilation subassembly 26 may be actuated and adjusted with adjustment knob 24' while monitoring pressure gauge 25', and observing patient's chest rise during ventilation.

Using the anterior and posterior electrodes, effective monitoring of the electrical activity of the heart is provided. In general, the closer the electrodes are to the heart, the stronger the EKG signals are that are received from the heart and the higher the signal to noise ratio of these signals. Although these signals may be slightly distorted by the activity of the CPR unit, these signals are strong and clear enough to detect gross arrhythmias such as ventricular fibrillation. Thus, effective monitoring of the electrical activity of the heart is achieved during normal operation of the supportive CPR unit.

Figure 8:
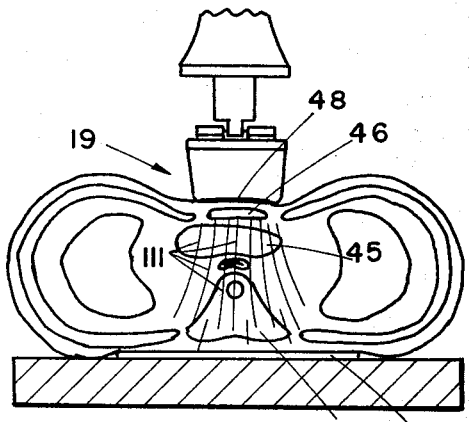
FIG. 8 is a sectional view of the apparatus of the present invention and the human body taken along line VII—VII of FIG. 6, except that the cross section is illustrated in a systole portion of the compressor cycle.

When a gross arrhythmia, such as ventricular fibrillation is detected and it is desirable to apply a defibrillation shock to the heart, the combination of the anterior electrode 48 and the posterior electrode 75 provides a short, direct electrical path through the heart, substantially reducing the amount of power required to defibrillate the heart. Referring now also to FIGS. 7 and 8, it is illustrated that this electrical path is further shortened by the action of cardiac compression. Referring now specifically to FIG. 7, the compressor pad 19 is illustrated in the diastole position or fully retracted position and the uncompressed heart is illustrated at 45. With reference now to FIG. 8 it is illustrated that by synchronizing defibrillation shock with the systole portion of the compression cycle, the action of the compressor substantially shortens the electrical path through the heart, compressing the heart between the sternum 46 and the backbone 112, between anterior electrode 48 and posterior electrode 75. Synchronizing the application of defibrillating shock with the systole portion of the compression cycle also compresses the anterior and posterior electrodes 48 and 75 against the chest and back, respectively, of the patient to create good ohmic contact therebetween. Thus, in addition to providing a good monitoring path for the electrical activity of the heart during CPR, the present invention provides an improved electrical path for administration of electrical defibrillation shocks to the heart. This reduces the trauma of electrical defibrillation to the patient by allowing effective defibrillation at reduced levels of total current and thus total electrical energy applied to the patient's body and heart.

Returning specifically now to the description of the operation of the present invention, if, while monitoring the electrical activity of the patient's heart, a gross arrhythmia, such as ventricular fibrillation is detected, the operator may apply definitive therapy such as defibrillation shock to the patient's heart by simply actuating a manual push button on the defibrillator, the manual push button corresponding to the paddle buttons normally provided on conventional defibrillator paddles. These paddle buttons would simply be depressed until the series wired synchronizing pressure switch 105 closes, determining that a systolic portion of the compression cycle has been reached and triggering the defibrillation shock. Preferably, the monitor would be temporarily disconnected from the defibrillating electrodes during defibrillation. This can be accomplished by making the switches 102 and 103 automatically actuable by the manually actuable defibrillator push button. As soon as the defibrillation shock has been applied, the monitor may be returned to operation and as the residual effects of the defibrillation shocks subside, an accurate picture of the electrical activity of the patient's heart should again appear.

The switch 105 will generally be adjustable such that the operator may precisely time the defibrillation shocks to the point of maximum compression of the CPR unit.

Alternatively, the pressure sensitive switch 105 may be set to sense the initiation of systole. In this case the switch 105 would be sensitive to lower pressures in the compressor cylinder and would be used in conjunction with a time delay relay to synchronize the application of a defibrillation shock with the point of maximum compression of the CPR unit. Time delay relays are commercially available items and many defibrillator units now in use include such a relay for synchronizing the application of defibrillation shocks with a specific portion of the patient's EKG trace. For example, with the compressor cycle now used on the CPR unit of the present invention, if the initiation of systole was sensed by pressure switch 105, a time delay relay which delayed the application of a defibrillation shock for approximately 0.35 seconds, would serve to accurately synchronize the defibrillation shock with the point of near maximum compression.

Although the operation of the CPR unit need not vary, since it is now being used in conjunction with an electric defibrillator, there are ongoing studies on the state of the art of external cardiac compression, and it may be that more optical frequencies and dwell times than those employed presently may be achieved in the future. In particular, it is possible that the relationship of ventilation to compression will be optimized a bit differently than that presently used. However, there will always be a finite period of systole in which defibrillation could be accomplished according to the present invention. Because of the reduced power requirements of a defibrillator operated according to the present invention, it is possible to build defibrillators operating with lower power requirements. Thus, one of the major advantages of the present invention is that a defibrillator of small compact size and low power may be designed. The advantages in the portability and the reduction in cost of such a defibrillator should be self evident.

Furthermore, it should be evident that the apparatus of the present invention provides a unique arrangement for applying both supportive and definitive therapy to a patient in cardiac arrest. More specifically, the apparatus of the present invention provides for simultaneous external cardiac compression and ventilation of the patient while the electrical activity of the patient is continuously monitored for gross arrhythmias and defibrillating shocks are periodically applied directly through the heart's myocardium. Thus, the present invention in addition to improving monitoring techniques and reducing the trauma of defibrillation is unique in its combination of supportive and definitive therapy for cardiac arrest.

The above description should be considered as exemplary and that of the preferred embodiment only. The true spirit and scope of the present invention should be determined by reference to the appended claims. It is desired to include within the appended claims all modifications that come within the proper scope of the invention.

The embodiments of the invention in which an exclusive property or privilege is claimed are defined as follows:

1. A cardiac compressor and defibrillator comprising in combination:

a reciprocatable cardiac compressor means for cyclically compressing a patient's chest;

said compressor means including a base for positioning behind the patient's back posterior to the patient's heart;

said compressor means including a cardiac compressor pad for positioning anterior to the patient's heart, said compressor pad being actuated by said compressor means for compressing the patient's heart between said compressor pad and said base;

an anterior electrode disposed on said compressor pad for compression between said compressor pad and the patient's sternum;

a posterior electrode disposed on said base for compression between said base and the patient's back;

a cardiac defibrillator means connected to said anterior and posterior electrodes for establishing an electric current therebetween; and a means for synchronizing said defibrillator means and said compressor means whereby a defibrillating current is applied to the patient's heart only during compression of a patient's heart.

2. The cardiac compressor of claim 1 further including means for ventilating the patient's lungs.

3. The cardiac compressor of claim 1 wherein said compressor means and said means for ventilating the patient's lungs are pneumatically driven and controlled.

4. The cardiac compressor of claim 1 further including means for monitoring the electrical activity of the patient's heart.

5. The cardiac compressor of claim 1 wherein said means for synchronizing comprises means for sensing pressure applied to the patient's chest by said compressor means and disabling said defibrillator means until a predetermined pressure is reached.

6. The cardiac compressor of claim 5 wherein said means for sensing pressure comprises a pressure sensitive switch for disabling said defibrillator means until a predetermined pressure is reached.

7. The cardiac compressor of claim 6 wherein said defibrillator means is triggered by a manually activated switch said pressure sensitive switch being normally open and connected in series with said manually activated switch to prevent the application of a defibrillating current until a predetermined pressure is reached.

8. The cardiac compressor of claim 6 wherein said compressor means includes a power cylinder and piston; and said pressure sensitive switch is responsive to pressure in said power cylinder.

9. The cardiac compressor of claim 1 wherein said means for synchronizing comprises means for sensing the initiation of systole and a time delay relay for disabling said defibrillator means until a predetermined time period has passed.

10. The cardiac compressor of claim 1 wherein said compressor pad is pivotally mounted on said compressor means for accommodating patients with sternums having various angular orientations.

11. The cardiac compressor of claim 1 wherein said compressor pad is provided with a face in contact with the patient's chest, said face having an area several times greater than the normal heel of hand area applied to the patient's chest during manual CPR.

12. The cardiac compressor of claim 1 wherein said compressor pad comprises an elastomeric body having a face conformable to the patient's chest.

13. The cardiac compressor of claim 12 wherein said anterior electrode comprises a planar flexible metalized electrode secured to said face of said compressor pad.

14. The cardiac compressor of claim 13 wherein said anterior electrode presents a contact area of 5 square inches or more with the patient's chest.

15. The cardiac compressor of claim 1 wherein said compressor pad comprises:
   a support connected to said compressor means;
   a body of semi-flexible elastomer mounted on said support;
   a face molded into said body, said face being molded to conform to a typical human chest, said body of semi-flexible elastomer accommodating variations in the size of each patient's chest.

16. The cardiac compressor of claim 15 wherein said anterior electrode comprises a mesh screen metal electrode vulcanized to said face of said compressor pad.

17. The cardiac compressor of claim 16 wherein a silver mesh screen is provided.

18. The cardiac compressor of claim 16 wherein a gold plated mesh screen is provided.

19. The cardiac compressor of claim 15 further including:
   an electrical terminal disposed on said support; and
   a plurality of flexible leads interconnecting said terminal and said anterior electrode.

20. The cardiac compressor of claim 19 wherein said flexible leads run internally in the body of said compressor pad.

21. The cardiac compressor of claim 15 wherein said support comprises a planar metal backing member for supporting said body.

22. The cardiac compressor of claim 21 wherein said planar metal backing member includes a hinge structure for pinning said compressor pad to said compressor means.

23. The cardiac compressor of claim 1 wherein said anterior electrode is integrally formed with said compressor pad said compressor pad being formed of a conductive material.

24. The cardiac compressor of claim 1 wherein said posterior electrode comprises a mesh screen metal electrode secured to the face of said base.

25. The cardiac compressor of claim 24 wherein a silver mesh screen is provided.

26. The cardiac compressor of claim 24 wherein a gold plated mesh screen is provided.

27. The cardiac compressor of claim 1 wherein said posterior electrode presents a contact area of 10 square inches or more with the patient's back.

28. The cardiac compressor of claim 1 wherein said posterior electrode is integrally formed with said base and said posterior electrode is electrically insulated from the rest of the cardiac compressor unit.

29. A cardiopulmonary resuscitator and defibrillator comprising in combination:
   a reciprocatable cardiac compressor means for cyclically compressing a patient's chest;
   said compressor means including a base for positioning behind the patient's back posterior to the patient's heart;
   said compressor means including a cardiac compressor pad for positioning anterior to the patient's heart, said compressor pad being actuated by said compressor means for compressing the patient's heart;
   an anterior electrode disposed on said compressor pad for compression between said compressor pad and the patient's sternum;
   a posterior electrode disposed on said base for compression between said base and the patient's heart;
   a means for ventilating the patient's lungs;
   a cardiac defibrillator means connected to said anterior and posterior electrodes for establishing an electric potential therebetween;
   a pressure sensitive switch for sensing pressure applied to the patient's heart by said compressor means, said switch synchronizing said defibrillator means and said compressor means, whereby a defibrillating current is applied to the patient's heart only during a systolic portion of a compression cycle of said compressor means; and
   a means for monitoring the electrical activity of the patient's heart connected to said anterior and posterior electrodes.

* * * * *